US010300229B2

(12) United States Patent
Djupesland et al.

(10) Patent No.: US 10,300,229 B2
(45) Date of Patent: May 28, 2019

(54) NASAL DELIVERY DEVICES

(71) Applicant: OPTINOSE AS, Oslo (NO)

(72) Inventors: Per Gisle Djupesland, Oslo (NO);
Michael Leclerc, Cranston, RI (US);
Ramy A. Mahmoud, Skillman, NJ
(US); Shane Siwinski, Providence, RI
(US); Joseph Gordon, Mansfield, MA
(US); Justin Fisk, Providence, RI (US)

(73) Assignee: OptiNose AS, Oslo (NO)

( * ) Notice: Subject to any disclaimer, the term of this patent is extended or adjusted under 35 U.S.C. 154(b) by 862 days.

(21) Appl. No.: 14/380,827

(22) PCT Filed: Feb. 25, 2013

(86) PCT No.: PCT/EP2013/053746
§ 371 (c)(1),
(2) Date: Aug. 25, 2014

(87) PCT Pub. No.: WO2013/124491
PCT Pub. Date: Aug. 29, 2013

(65) Prior Publication Data
US 2015/0013670 A1    Jan. 15, 2015

Related U.S. Application Data

(60) Provisional application No. 61/603,095, filed on Feb. 24, 2012.

(51) Int. Cl.
*A61M 15/08*    (2006.01)
*A61M 15/00*    (2006.01)

(52) U.S. Cl.
CPC .......... *A61M 15/08* (2013.01); *A61M 15/002* (2014.02); *A61M 15/009* (2013.01);
(Continued)

(58) Field of Classification Search
CPC .... A61M 11/00; A61M 11/006; A61M 11/08; A61M 15/00; A61M 15/0001;
(Continued)

(56) References Cited

U.S. PATENT DOCUMENTS 605,436 A    6/1898  Kellogg
642,748 A    2/1900  Manners
(Continued)

FOREIGN PATENT DOCUMENTS

CN      1258223 A     6/2000
CN    101056666 A    10/2007
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — (Jackie) Tan-Uyen T Ho
*Assistant Examiner* — Joseph D Boecker
(74) *Attorney, Agent, or Firm* — Finnegan, Henderson, Farabow, Garrett & Dunner, LLP

(57) ABSTRACT

A nasal delivery device for and method of delivering substance to a nasal airway of a subject, the delivery device comprising: a nosepiece (117) for fitting to a nasal cavity of a subject; a mouthpiece (119) into which the subject in use exhales; a delivery unit, which comprises an actuation part which is manually displaceable to actuate the delivery unit to deliver substance from the nosepiece; and a valve assembly (127) which is fluidly connected to the nosepiece and the mouthpiece, wherein the valve assembly comprises a body element (128) and a valve element (131) which is movably disposed to the body element between closed and open configurations by manual displacement of the actuation part
(Continued)

of the delivery unit to provide for an air flow through the nosepiece simultaneously with delivery of substance.

43 Claims, 11 Drawing Sheets

(52) U.S. Cl.
CPC .... *A61M 15/0018* (2014.02); *A61M 15/0021* (2014.02); *A61M 15/0098* (2014.02); *A61M 2210/0618* (2013.01)

(58) Field of Classification Search
CPC .......... A61M 15/0013; A61M 15/0018; A61M 15/002; A61M 15/0021; A61M 15/009; A61M 15/0093; A61M 15/0096; A61M 15/0098; A61M 15/08; A61M 2210/0618; A61M 2210/0625; A61M 2205/076
USPC ...... 222/402.1, 162, 635, 145.1; 128/200.14, 128/200.21–200.23, 203.18, 128/203.22–203.24
See application file for complete search history.

(56) References Cited

U.S. PATENT DOCUMENTS

| | | |
|---|---|---|
| 746,749 A | 12/1903 | Seidel |
| 3,636,949 A * | 1/1972 | Kropp ............... A61M 15/0091 128/200.23 |
| 5,797,392 A | 8/1998 | Keldmann et al. |
| 6,648,848 B1 | 11/2003 | Keldmann et al. |
| 6,715,485 B1 | 4/2004 | Djupesland |
| D530,815 S | 10/2006 | Murphy et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 6/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2006/0289007 A1* | 12/2006 | Williams .......... A61M 15/0091 128/203.15 |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0173301 A1* | 7/2008 | Deaton ............... A61M 15/009 128/203.12 |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0199984 A1* | 8/2010 | Williams, III .... A61M 15/0065 128/200.23 |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2010/0308082 A1 | 12/2010 | Lamble et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0120456 A1* | 5/2011 | Immel ............... A61M 15/0085 128/200.23 |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |

(56) References Cited

U.S. PATENT DOCUMENTS

| | | |
|---|---|---|
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |

FOREIGN PATENT DOCUMENTS

| | | |
|---|---|---|
| CN | 101918061 A | 12/2010 |
| GB | 2471973 | 1/2011 |
| JP | 2001-526577 A | 12/2001 |
| JP | 2010-540147 A | 12/2010 |
| WO | WO 96/22802 | 8/1996 |
| WO | WO 98/53869 | 12/1998 |
| WO | WO 00/51672 | 9/2000 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/001585 A1 | 1/2007 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

* cited by examiner

NASAL DELIVERY DEVICES

The present invention relates to a nasal delivery device for and a method of delivering a substance, in particular one of a liquid, as a suspension or solution, or a powder, such as containing a medicament, especially systemic or topical pharmaceuticals, or a vaccine, to the nasal airway of a subject.

Referring to FIG. 10, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and anti-biotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-2000/051672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide nasal delivery devices and methods for delivering substances to a nasal cavity of subject, and in particular relatively-simple mechanically-actuatable delivery devices.

In one aspect the present invention provides a nasal delivery device for delivering substance to a nasal airway of a subject, comprising: a nosepiece for fitting to a nasal cavity of a subject; a mouthpiece into which the subject in use exhales; a delivery unit, which comprises an actuation part which is manually displaceable to actuate the delivery unit to deliver substance from the nosepiece; and a valve assembly which is fluidly connected to the nosepiece and the mouthpiece, wherein the valve assembly comprises a body element and a valve element which is movably disposed to the body element between closed and open configurations by manual displacement of the actuation part of the delivery unit to provide for an air flow through the nosepiece simultaneously with delivery of substance.

In another aspect the present invention provides a method of delivering substance to a nasal airway of a subject, comprising the steps of: fitting a nosepiece to a nasal cavity of a subject; the subject exhaling into a mouthpiece; providing a delivery device which comprises: a delivery unit, which comprises an actuation part which is manually displaceable to actuate the delivery unit to deliver substance from the nosepiece; and a valve assembly which is fluidly connected to the nosepiece and the mouthpiece, wherein the valve assembly comprises a body element and a valve element which is movably disposed to the body element between closed and open configurations by manual displacement of the actuation part of the delivery unit; and manually displacing the actuation part of the delivery unit to move the valve element of the valve assembly relative to the body element of the valve assembly between closed and open configurations and provide an air flow through the nosepiece simultaneously with delivery of substance.

Preferred embodiments of the present invention will now be described hereinbelow by way of example only with reference to the accompanying drawings, in which:

FIGS. 1(*a*) and (*b*) illustrate a perspective view of a nasal delivery device in accordance with a first embodiment of the present invention;

Figure 1A:
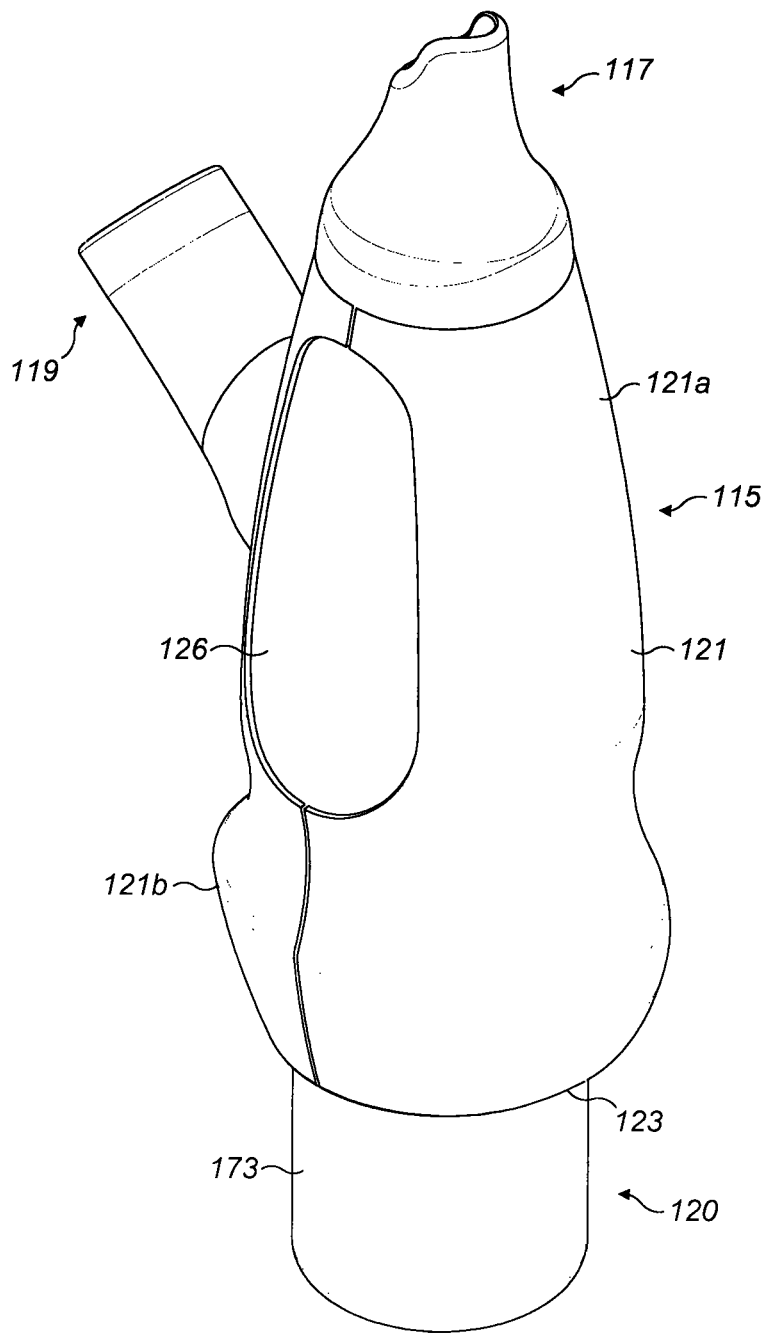
Figure 1B:
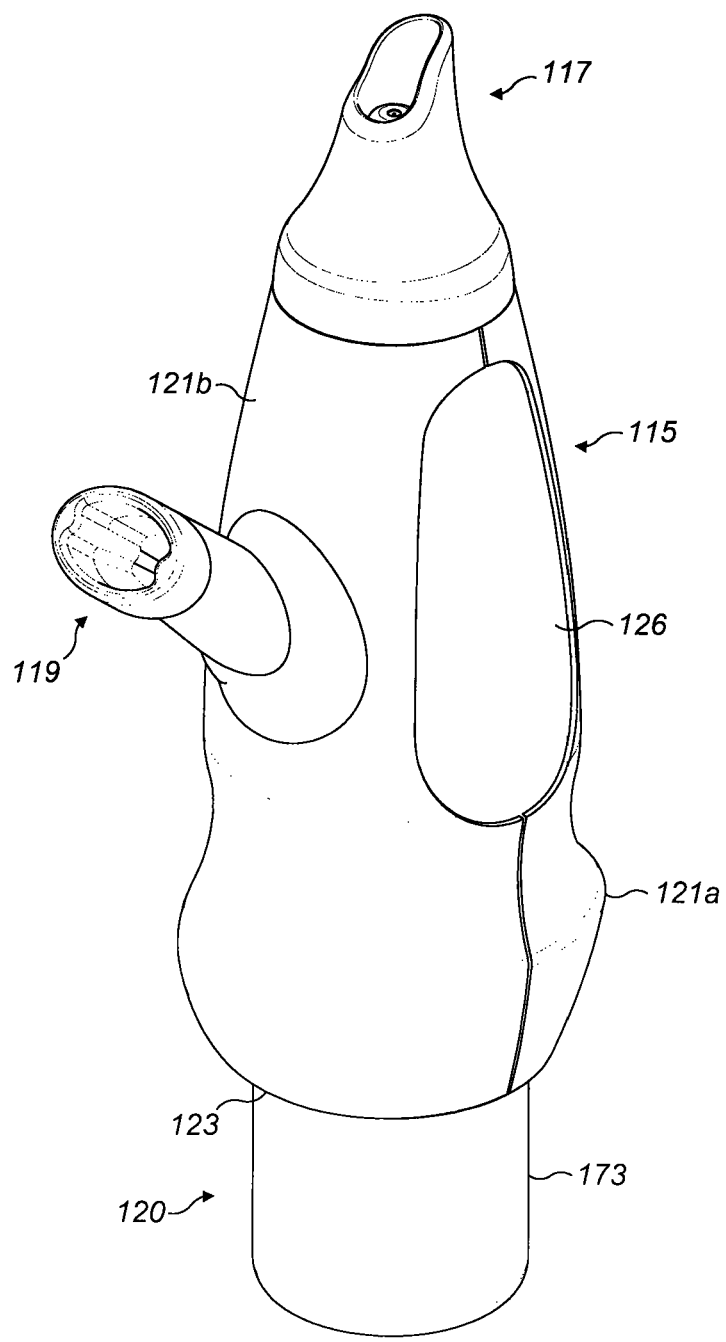
Figure 2:
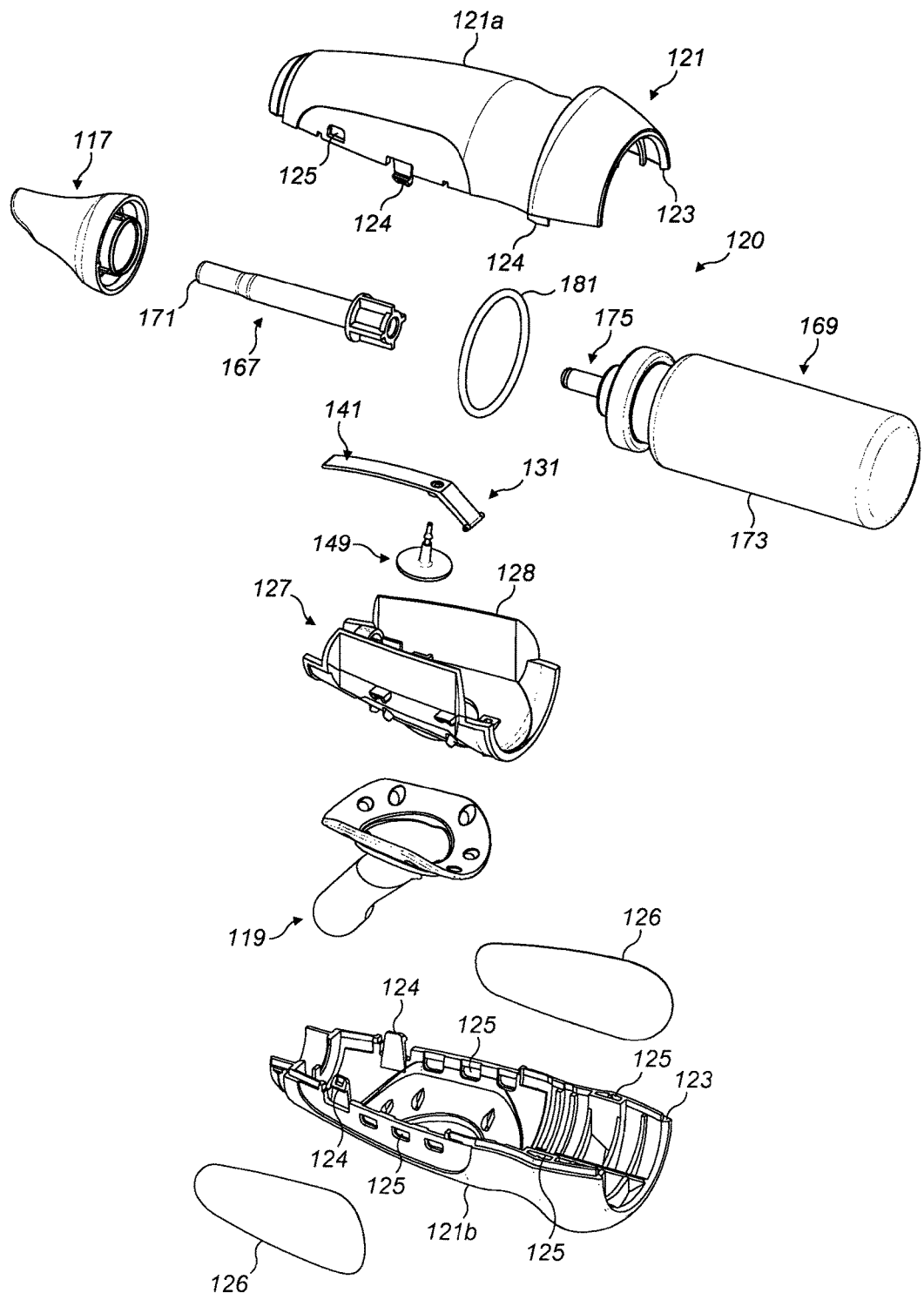
FIG. 2 illustrates an exploded perspective view of the delivery device of FIG. 1.
Figure 3:
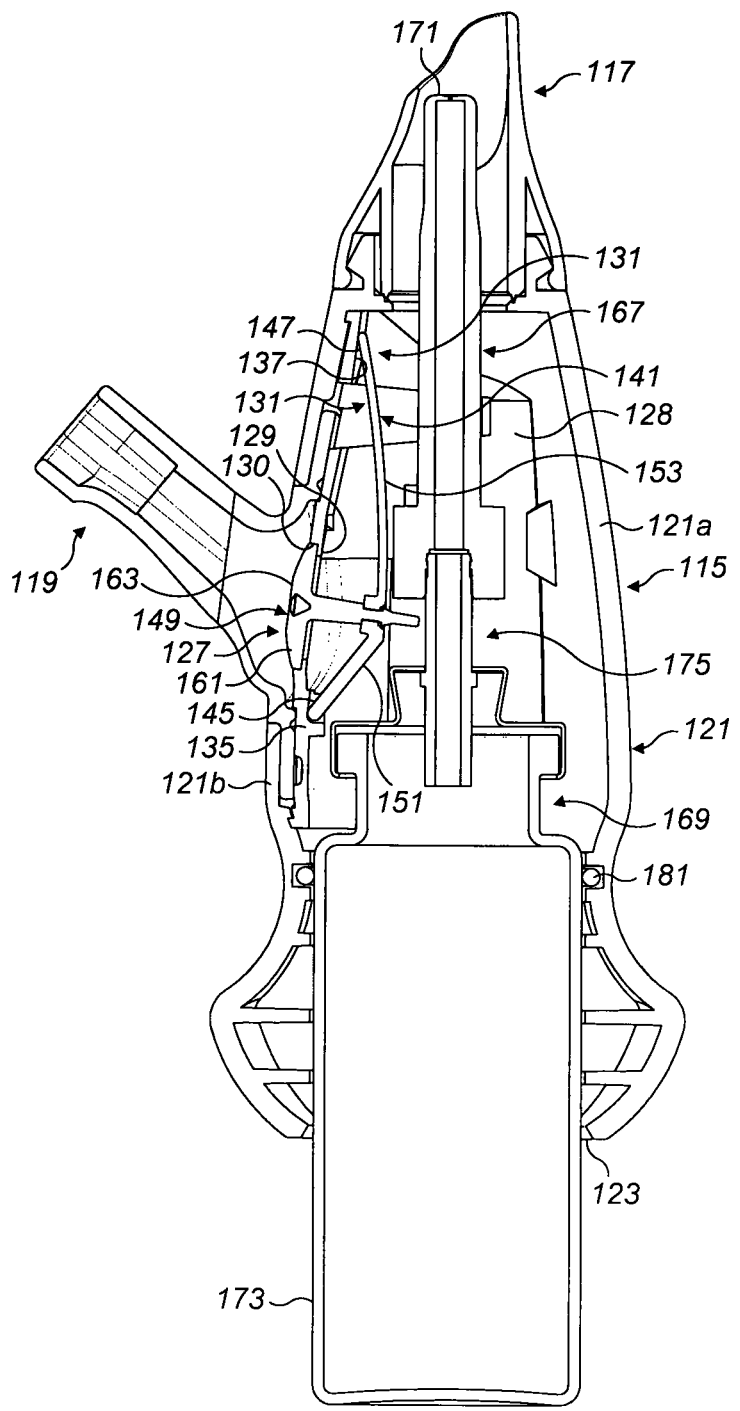
FIG. 3 illustrates a vertical sectional view of the delivery device of FIG. 1, in the at rest, non-actuated configuration.
Figure 4:
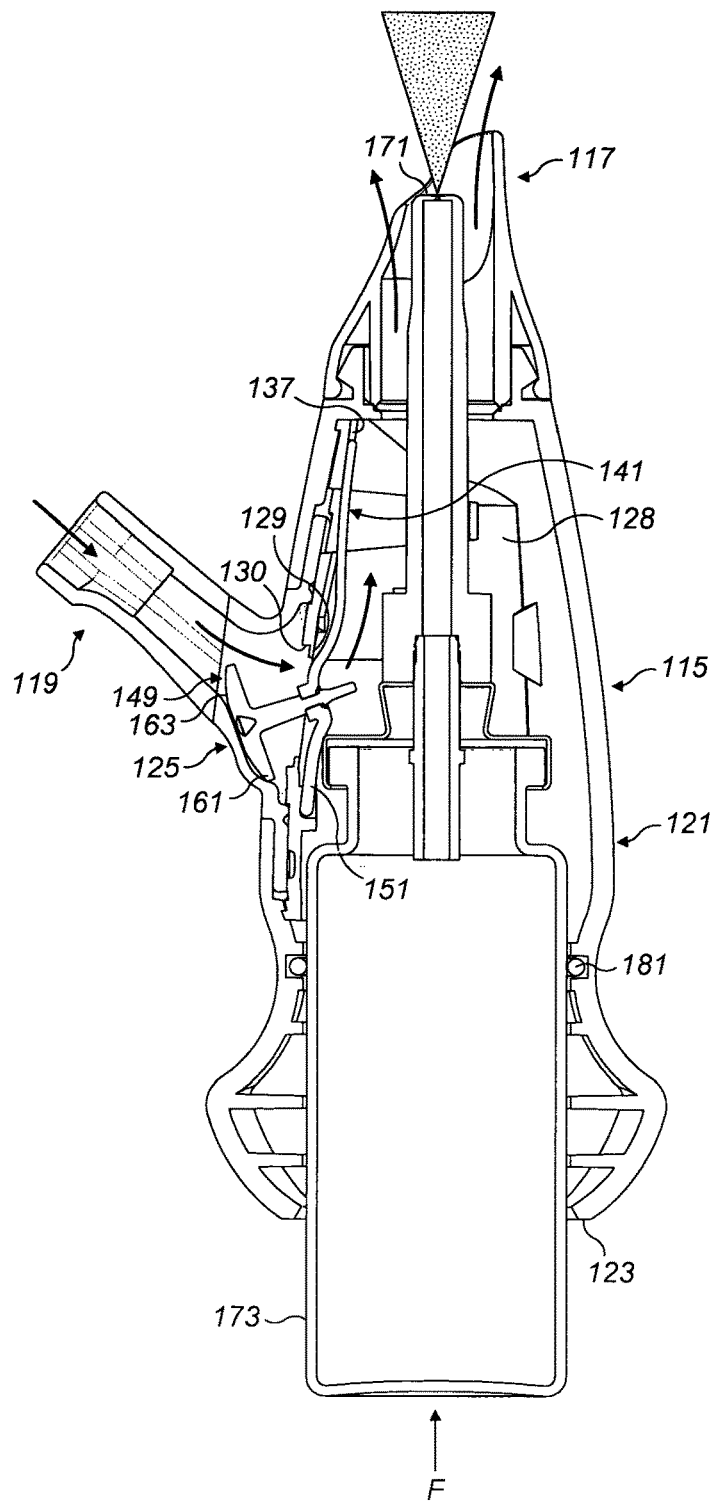
FIG. 4 illustrates a vertical sectional view of the delivery device of FIG. 1, in the actuated configuration.
Figure 5:
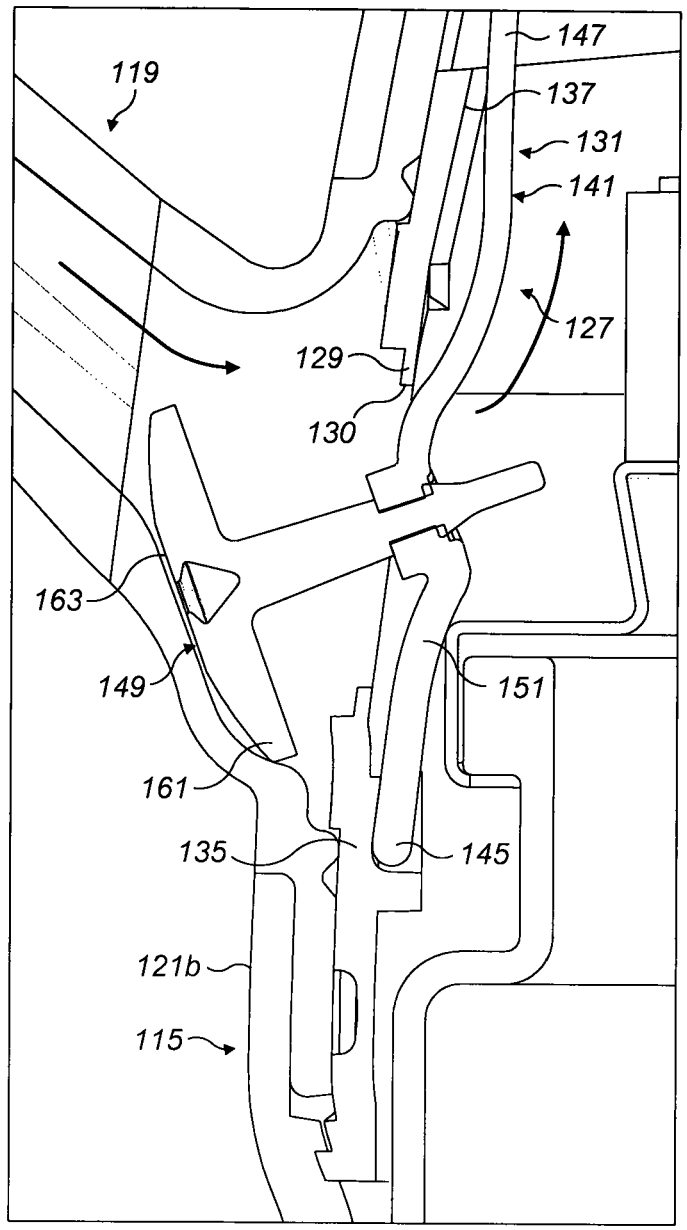
FIG. 5 illustrates an exploded, fragmentary vertical sectional view of the delivery device of FIG. 1, in the actuated configuration.
Figure 7:
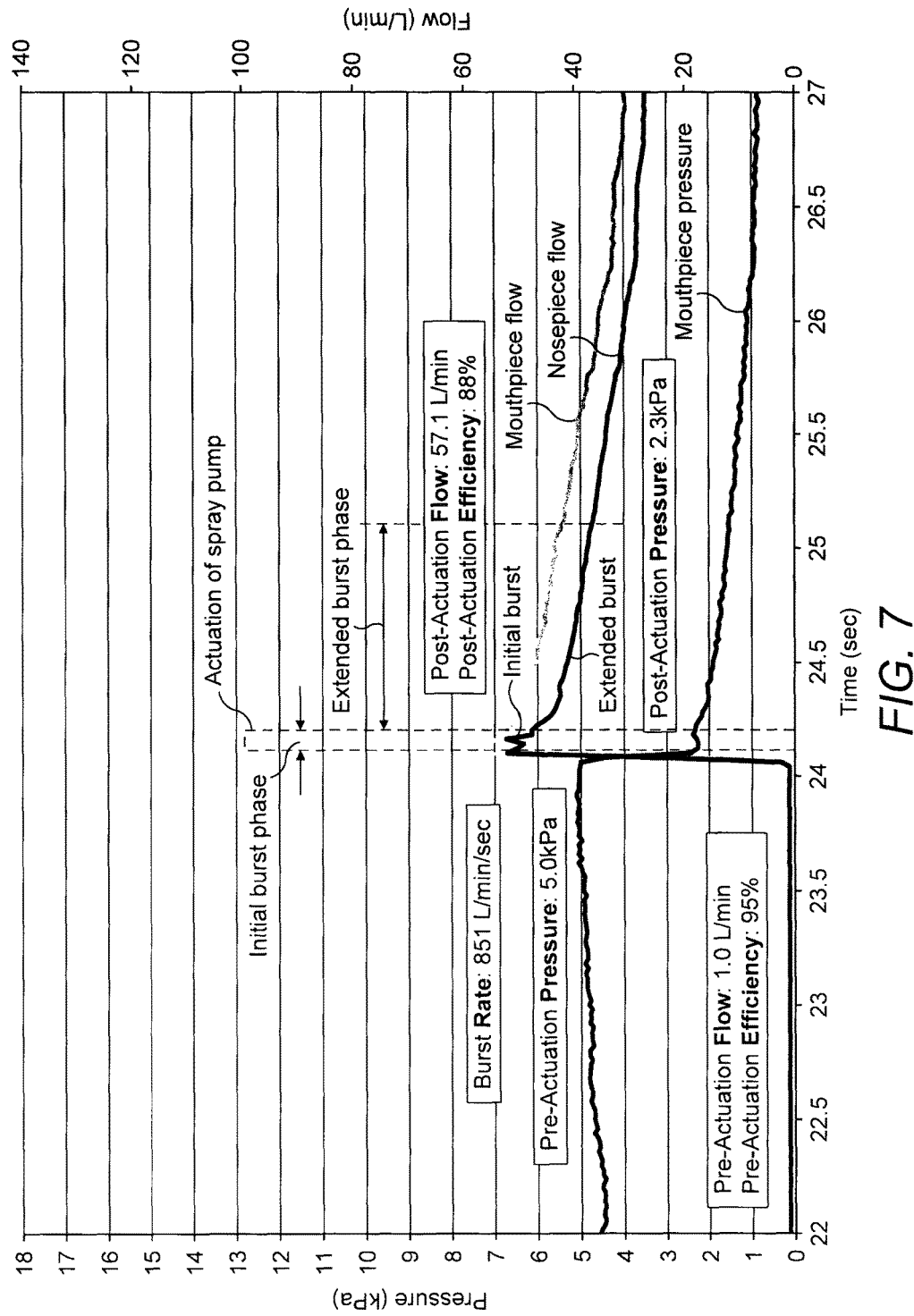
Figure 8A:
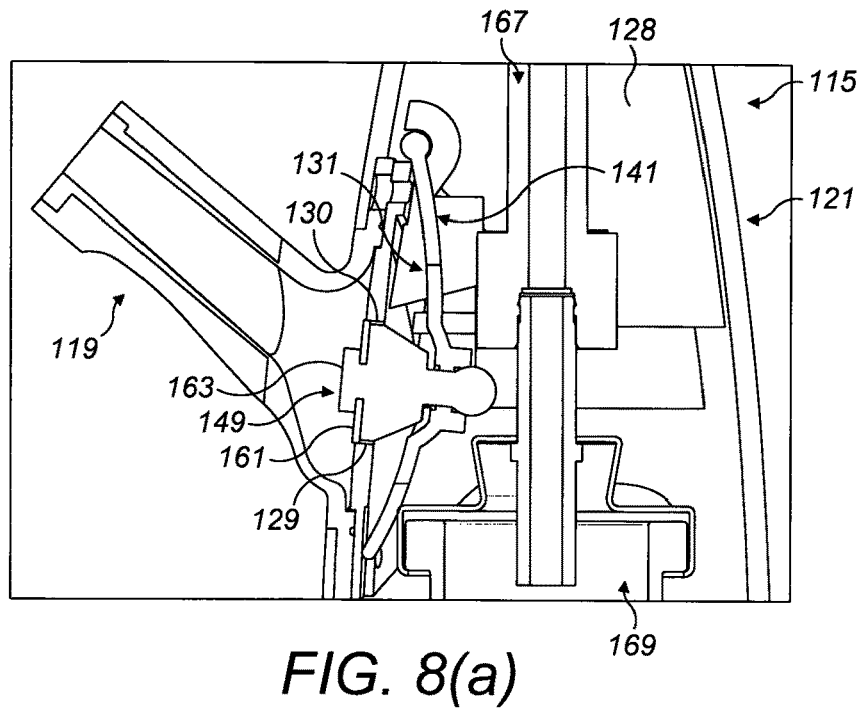
Figure 8B:
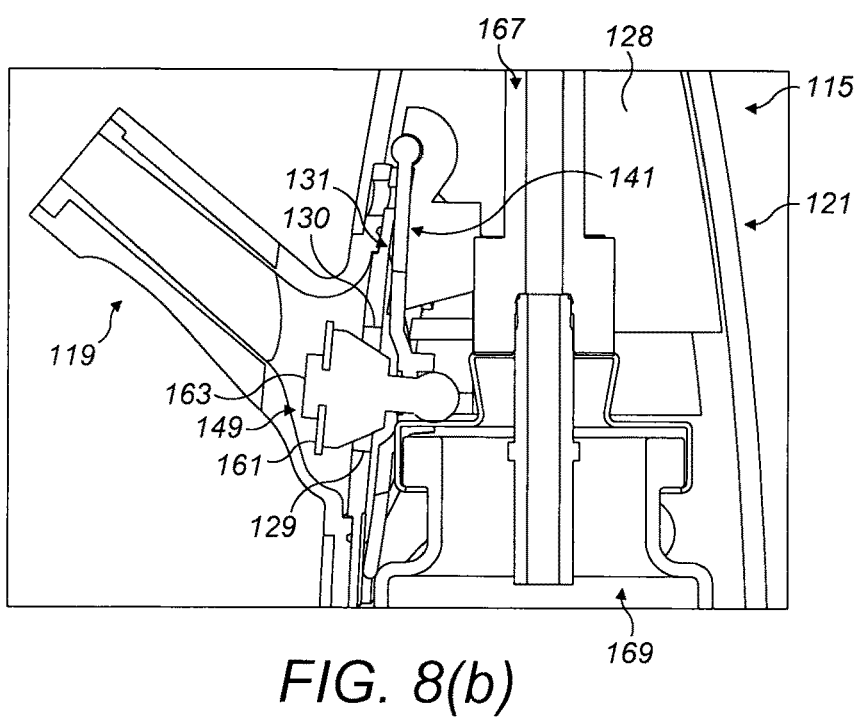
Figure 9A:
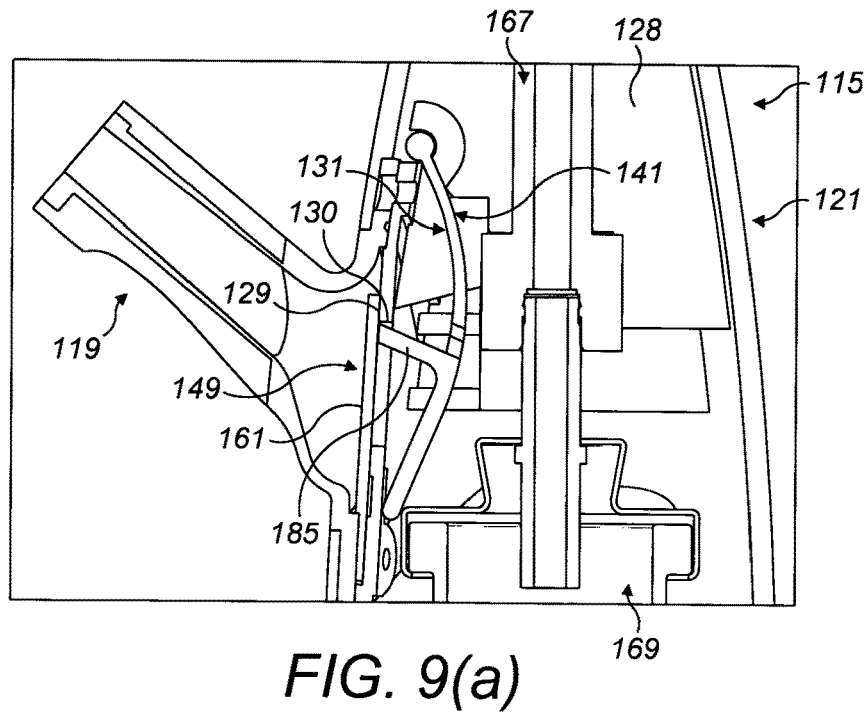
Figure 9B:
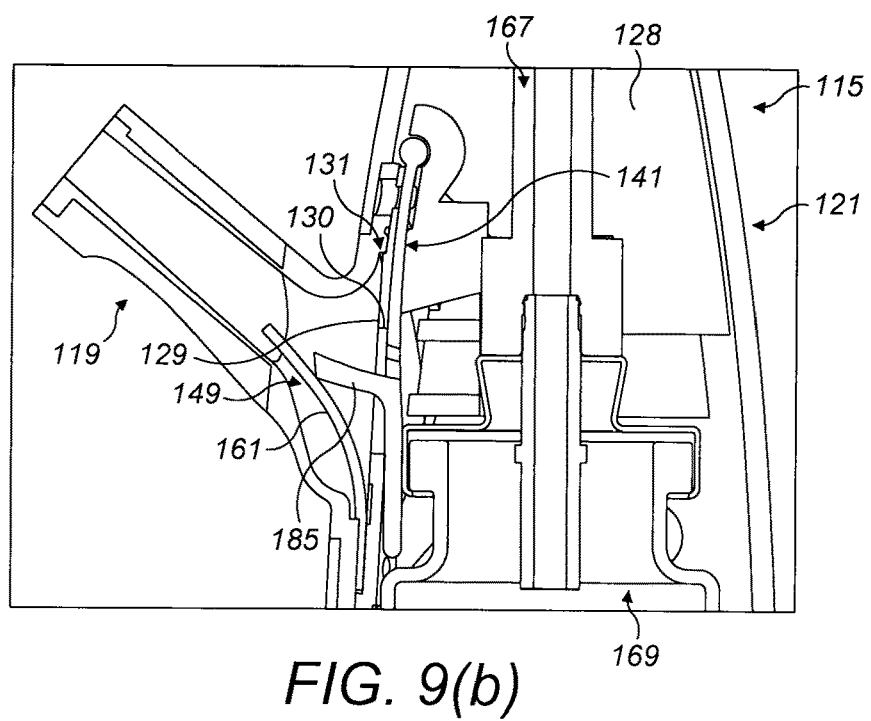
Figure 10:
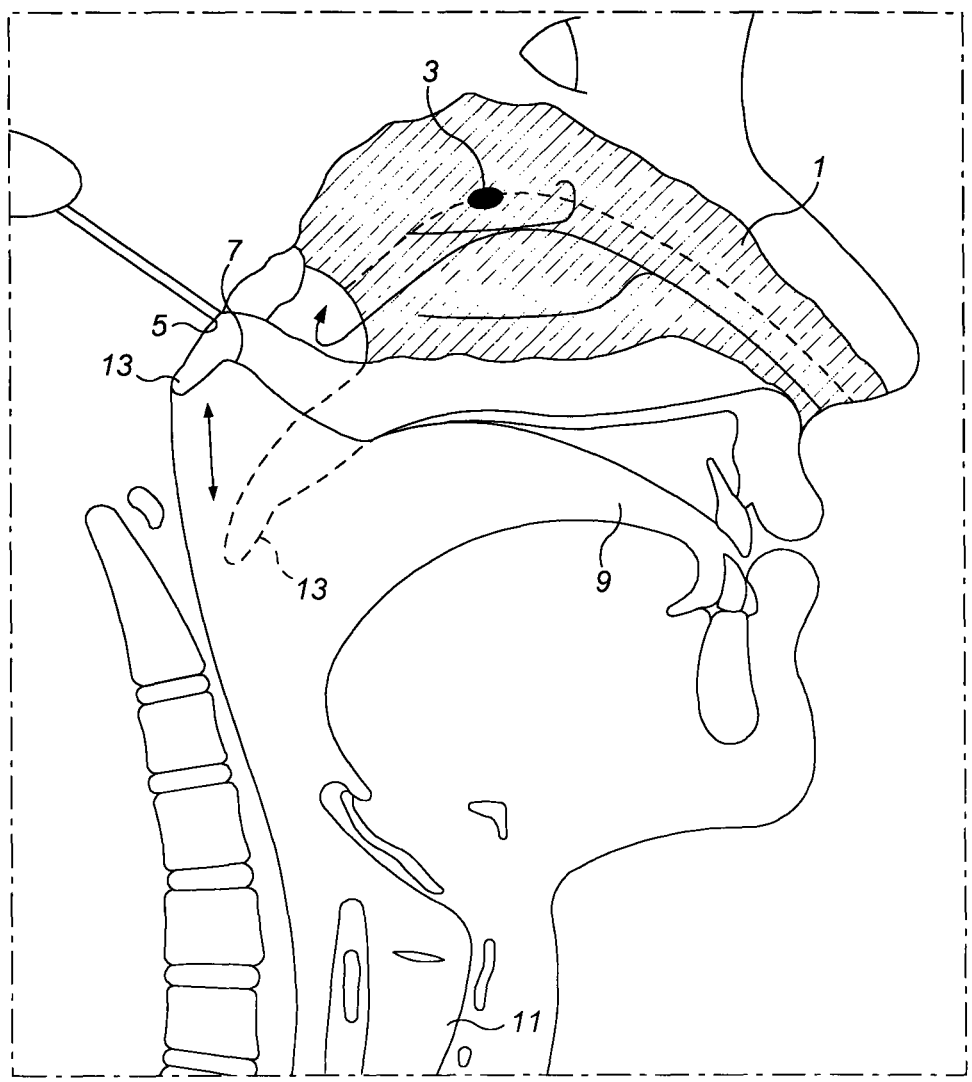

FIGS. 6(*a*) to (*c*) illustrate the opening of the sealing member of the valve assembly by operation of the delivery unit of the delivery device of FIG. 1;

FIG. 7 illustrates plots of the flow rates at the nosepiece and the mouthpiece and the pressure at the mouthpiece for one exemplary device;

FIGS. 8(*a*) and (*b*) illustrate fragmentary vertical sectional views in the at rest, non-actuated and actuated configurations of a nasal delivery device in accordance with a second embodiment of the present invention;

FIGS. 9(*a*) and (*b*) illustrate fragmentary vertical sectional views in the at rest, non-actuated and actuated configurations of a nasal delivery device in accordance with a third embodiment of the present invention; and FIG. 10 schematically illustrates the anatomy of the upper respiratory tract of a human subject.

FIGS. 1 to 7 illustrate a manually-actuated nasal delivery device in accordance with a first embodiment of the present invention.

Figure 6C:
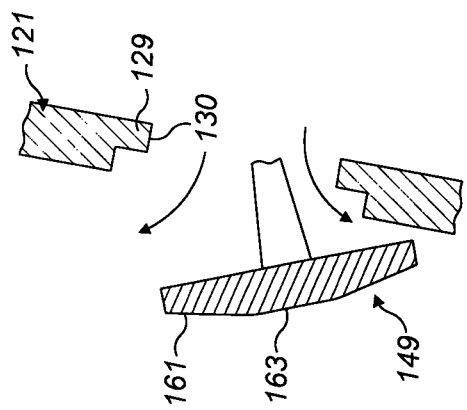
Figure 6B:
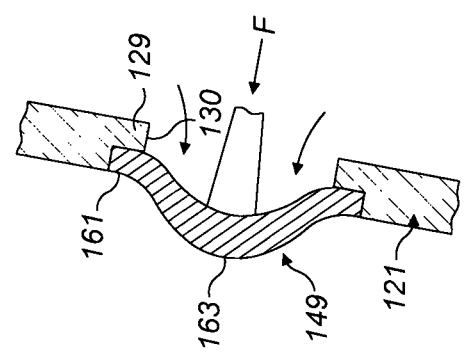
Figure 6A:
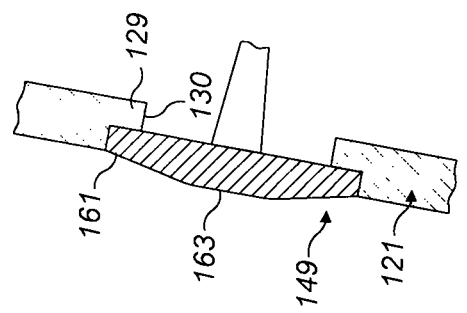

The delivery device comprises a housing 115, a nosepiece 117 for fitting in a nasal cavity of a subject, a mouthpiece 119 into which the subject in use exhales, such as to enable delivery of an air flow into and through the nasal airway of the subject on exhalation by the subject through the mouthpiece 119, and a delivery unit 120, which is manually actuatable to deliver substance to the nasal cavity of the subject.

The housing 115 comprises a body member 121, in this embodiment of substantially elongate, tubular section which includes an aperture 123 at one end thereof, through which projects an actuating part of the delivery unit 120, in this embodiment as defined by the base of a substance-containing chamber 173 of a substance-supply unit 169.

In this embodiment the body member 121 comprises two body sections 121*a, b* which are fixed together.

In this embodiment the body sections 121*a, b* include inter-engaging lugs 124 and detents 125, here of snap-fit type, and sealing elements 126, which act to close the air flow paths at the junctions of the body sections 121*a, b*.

In this embodiment the sealing elements 126 are adhesively bonded, but could alternatively be mechanically bonded, such as by welding.

In an alternative embodiment the sealing elements 126 could be omitted.

The housing 115 further comprises a valve assembly 127 which is fluidly connected to the nosepiece 117 and the mouthpiece 119, and operable between closed and open configurations, as illustrated in FIGS. 3 and 4, such as to provide for an air flow, in this embodiment in the form of a burst of air, through the nosepiece 117 simultaneously with actuation of the delivery unit 120, as will be described in more detail hereinbelow.

The valve assembly 127 comprises a main, body element 128 which includes a valve seat 129 defining a valve opening 130, and a valve element 131 which is movably disposed to the body element 128 between closed and open positions, as illustrated in FIGS. 3 and 4.

As particularly illustrated in FIG. 3, the body element 128 comprises a pivot 135, in this embodiment to one, lower side of the valve seat 129, to which one end 145 of the valve element 131 is pivoted, and a sliding surface 137, in this embodiment to the other, upper side of the valve seat 129, against which the other end 147 of the valve element 131 is slideable.

The valve element 131 comprises an elongate arm 141, in this embodiment a flexible arm, one end 145, in this embodiment the lower end, of which is pivoted to the pivot 135 of the body element 128, and the other, upper end 147 of which slideably engages the sliding surface 137 of the body element 128, and a valve member 149 which is supported by the arm 141.

In this embodiment the arm 141 comprises a first, here lower, arm section 151, which is biased, here inwardly, such that, when the valve element 131 is in the closed, rest position, the lower arm section 151 is inclined inwardly relative to the longitudinal axis of the housing 115 and engageable by the substance-supply unit 169 when manually actuated to move the valve element 131 to the open position, as will be described in more detail hereinbelow. In some embodiments, the first arm section may comprise a substantially rigid section.

In this embodiment the arm 141 further comprises a second, here upper, arm section 153, which engages the sliding surface 137 of the body element 128 and acts to bias the valve element 131 to the closed position.

In this embodiment the valve member 149 comprises a seal 161, in this embodiment a flexible or resilient element, which acts to close the valve opening 130 as defined by the valve seat 129 when the valve element 131 is in the closed position, and a support 163 which supports a central region of the seal 161.

With this configuration, and referring to FIGS. 6(a) to (c), where the seal 161 is centrally supported, when the valve element 131 is moved to the open position, the support 163 biases the central region of the seal 161, as illustrated in FIG. 6(b), causing the seal 161 to bulge outwardly in this central region and thus provide that the seal 161 engages the valve seat 129 only at the peripheral edge of the seal 161, until the point is reached when the seal 161 is suddenly and explosively released from the valve seat 129, as illustrated in FIG. 6(c).

This mode of release is believed to be particularly effective in the present application where it is desired to achieve a sudden, initial burst of air flow, in that substantially the entire sealing surface of the seal 161 is released in one instant, which compares to an alternative mode of a peeling-type release, where a smaller section of a sealing surface is released, followed by the remainder of the sealing surface, which tends to provide a smaller initial burst pressure.

In this embodiment the delivery unit 120 comprises an outlet unit 167 for delivering substance into the nasal airway of the subject, and a substance-supply unit 169 for delivering substance to the outlet unit 167.

In this embodiment the valve assembly 127 provides for a pre-actuation efficiency of less than 5 L/min when a user is developing an exhalation pressure of 3 kPa, preferably less than 5 L/min when a user is developing an exhalation pressure of 10 kPa, more preferably less than 1 L/min when a user is developing an exhalation pressure of 3 kPa, still more preferably less than 1 L/min when a user is developing an exhalation pressure of 10 kPa, yet more preferably substantially no flow when a user is developing an exhalation pressure of 3 kPa, and still yet more preferably substantially no flow when a user is developing an exhalation pressure of 10 kPa; the pre-actuation efficiency being a measure of the volume of air which escapes from the device prior to actuation as a fraction of the volume of air delivered into the mouthpiece 119.

In this embodiment the delivery device is configured to provide a post-actuation efficiency of at least 80% at a flow rate of 50 L/min and an exhalation pressure of 3 kPa, preferably at least 85% at a flow rate of 50 L/min and an exhalation pressure of 3 kPa, more preferably at least 88% at a flow rate of 50 L/min and an exhalation pressure of 3 kPa, and yet more preferably at least 90% at a flow rate of 50 L/min and an exhalation pressure of 3 kPa; the post-actuation efficiency being a measure of the volume of air delivered from the nosepiece 117 as a fraction of the volume of air delivered into the mouthpiece 119.

FIG. 7 illustrates, for one exemplary device, plots of the flow rates at the nosepiece 117 and the mouthpiece 119 and the pressure at the mouthpiece 119.

In this embodiment the pre-actuation efficiency of 1 L/min at a pre-actuation pressure of 5 kPa.

In this embodiment the post-actuation efficiency is 88% at a flow rate of 57.1 L/min.

In this embodiment, the valve element 131 provides for a burst of air flow on opening thereof, having a first, initial burst phase followed by a second, extended burst phase, wherein the peak flow rate in the initial burst phase has a higher flow rate than the average flow rate in the extended burst phase, and the extended burst phase is of substantially greater duration than the initial burst phase.

In this embodiment the peak flow rate in the initial burst phase is at least 10%, preferably at least 15%, and more preferably at least 20%, greater than that of the average flow rate of the extended burst phase in a period corresponding to ten times the duration of the period in which substance is delivered from the nosepiece 117 by the delivery unit 120.

In this embodiment the delivery unit 120 provides a spray which commences 54 ms after opening of the sealing member 149 and terminates 134 ms after opening of the sealing member 149.

In one embodiment the delivery unit 120 provides for delivery of substance subsequent to opening of the sealing member 149.

In one embodiment the delivery unit 120 provides for delivery of substance in a period less than about 250 ms from opening of the sealing member 149, preferably less than about 200 ms from opening of the sealing member 149, more preferably less than about 150 ms from opening of the sealing member 149, and still more preferably more preferably less than about 100 ms from opening of the sealing member 149.

In one embodiment the delivery unit 120 provides for delivery of substance commencing less than about 150 ms subsequent to opening of the sealing member 149, preferably less than about 100 ms subsequent to opening of the sealing member 149, still more preferably less than about 50 ms subsequent to opening of the sealing member 149, yet more preferably less than about 25 ms subsequent to opening of the sealing member 149, still more preferably less than about 15 ms subsequent to opening of the sealing member 149.

In this embodiment the outlet unit 167 comprises a nozzle 171 for delivering substance to the nasal airway of the subject. In this embodiment the nozzle 171 is configured to provide an aerosol spray. In an alternative embodiment, for the delivery of a liquid, the nozzle 171 could be configured to deliver a liquid jet as a column of liquid.

In a preferred embodiment the distal end of the outlet unit 167 is configured to extend at least about 2 cm, preferably at least about 3 cm, and more preferably from about 2 cm to about 3 cm, into the nasal cavity of the subject.

In this embodiment the substance supply unit 169 is a pump unit, which comprises a substance-containing chamber 173 which contains substance and extends from the aperture 123 in the housing 115 as the actuating part of the substance-supply unit 169, and a mechanical delivery pump 175 which is actuatable, here by depression of the substance-containing chamber 173, typically by a finger or thumb of the subject, to deliver a metered dose of substance from the substance-containing chamber 173 to the outlet unit 167 and from the nozzle 171 thereof, here as an aerosol spray.

In this embodiment the substance-containing chamber 173, when depressed to actuate the substance supply unit 169, engages the lower arm section 151 of the arm 141 of the valve element 131, such as simultaneously to provide for actuation of the substance-supply unit 169 and opening of the seal 161 of the valve element 131, whereby substance, here in the form of a spray, and an air flow, here as a burst of air, are simultaneously delivered to the nasal cavity of the subject.

In this embodiment the mechanical delivery pump 175 is a liquid delivery pump for delivering a metered dose of substance, but in an alternative embodiment the mechanical delivery pump 175 could be a powder delivery pump, which delivers metered doses of a powdered substance on actuation thereof.

In this embodiment the substance-supply unit 169 is a multi-dose unit for delivering a plurality of metered doses of substance in successive delivery operations.

In an alternative embodiment the substance-supply unit 169 could be a single-dose unit for delivering a single metered dose of substance or a duo-dose unit for delivering two metered doses of substance in two successive delivery operations.

In another alternative embodiment the substance-supply unit 169 could comprise a dry powder delivery unit which delivers metered doses of a substance, as a dry powder, on actuation thereof.

In yet another alternative embodiment the substance-supply unit 169 could comprise a nebulizer which delivers metered doses of a substance, as an aerosol spray, on actuation thereof.

In still another alternative embodiment the substance-supply unit 169 could comprise an aerosol canister for delivering metered volumes of a propellant, preferably a hydrofluoroalkane (HFA) propellant or the like, containing substance, either as a suspension or solution.

In this embodiment the housing 115 further comprises a sealing member 181, here an annular seal, in the form of an O-ring, which slideably receives the substance-containing chamber 173 of the substance-supply unit 169, such as to prevent the escape of the delivered air flow from the aperture 123 in the housing 115.

In one embodiment the sealing member 181 could be omitted.

FIGS. 8(*a*) and (*b*) illustrate a nasal delivery device in accordance with a second embodiment of the present invention.

The delivery device of this embodiment is substantially the same as the delivery device of the first-described embodiment, and thus, in order to avoid unnecessary duplication of description, only the differences will be described in detail, with like parts being designated by like reference signs.

The delivery device of this embodiment differs from that of the first-described embodiment principally in that the valve member 149 is configured such that the support 163 extends across substantially the entire width of the valve opening 130. In this way, the seal 161 is not able to bulge in the manner of the above-described embodiment, and is instead opened by a peeling action. FIG. 8(*a*) illustrates the valve assembly 127 in the at rest, non-actuated configuration. FIG. 8(*b*) illustrates the valve assembly 127 in the actuated configuration.

FIGS. 9(*a*) and (*b*) illustrate a nasal delivery device in accordance with a third embodiment of the present invention.

The delivery device of this embodiment is very similar to the delivery device of the first-described embodiment, and thus, in order to avoid unnecessary duplication of description, only the differences will be described in detail, with like parts being designated by like reference signs.

The delivery device of this embodiment differs from that of the first-described embodiment principally in that the seal 161 is not supported by the arm 141, but is instead a separate element, which is displaced by movement of the arm 141, as caused by manual actuation of the substance-supply unit 169. FIG. 9(*a*) illustrates the valve assembly 127 in the at rest, non-actuated configuration. FIG. 9(*b*) illustrates the valve assembly 127 in the actuated configuration.

In this embodiment the seal 161 comprises a flexible element, here in the form of a flap, and in one embodiment a resilient element, which is engaged by an engagement element 185 on the arm 141.

In this embodiment the engagement element 185 comprises a projection which acts to cause the seal 161 to bulge in the manner of the first-described embodiment.

In an alternative embodiment the engagement element 185 could extend across substantially the width of the valve opening 130, causing the seal 161 to be moved from the valve seat 129 with a peeling action in a similar manner to the second-described embodiment.

Finally, it will be understood that the present invention has been described in its preferred embodiments and can be modified in many different ways without departing from the scope of the invention as defined by the appended claims.

The invention claimed is:

1. A nasal delivery device for delivering substance to a nasal airway of a subject, comprising;
a nosepiece for fitting to a nasal cavity of the subject;
a mouthpiece into which the subject in use exhales;
a mechanical delivery puma, which comprises an actuator which is manually displaceable to actuate the delivery pump to deliver substance from the nosepiece; and
a valve assembly which is fluidly connected to the nosepiece and the mouthpiece, wherein the valve assembly comprises a body element and a valve element movable relative to the body element between closed and open configurations by manual displacement of the actuator of the delivery pump to provide for an air flow through the nosepiece simultaneously with delivery of substance;
wherein the body element includes a pivot, and the valve element comprises an arm having a first end pivotally connected to the body element and configured to pivot between the closed and open configurations.

2. The delivery device of claim 1, wherein the arm is at least in part resilient.

3. The delivery device of claim 1, wherein the arm has a second end and the body element includes a sliding surface, against which the second end of the arm is slideable.

4. The delivery device of claim 1, wherein the arm comprises a first arm section, which is configured such that, when the valve element is in the closed configuration, the first arm section is engageable by displacement of the actuator of the delivery pump.

5. The delivery device of claim 4, wherein the arm is biased inwardly relative to a longitudinal axis of the delivery device.

6. The delivery device of claim 4, wherein the arm comprises a second arm section which engages the sliding surface of the body element.

7. The delivery device of claim 6, wherein the second arm section is a resilient section which acts to bias the valve element to the closed configuration.

8. The delivery device of claim 6, wherein the first and second arm sections enclose an obtuse angle.

9. The delivery device of claim 1, wherein the arm is inclined inwardly relative to a longitudinal axis of the delivery device when the valve element is in the closed configuration.

10. The delivery device of claim 1, wherein the body element includes a valve seat which defines a valve opening, and the valve element comprises a seal which acts to close the valve opening when the valve element is in the closed position.

11. The delivery device of claim 10, wherein the valve element comprises a support which supports a central region of the seal, such as to allow a peripheral region of the seal to engage the valve seat and the central region to be deflected relative to the peripheral region, thereby allowing for sudden release of the seal.

12. The delivery device of claim 10, wherein the valve element comprises a support which extends substantially across a width of the valve opening.

13. The delivery device of claim 10, wherein the seal is separate to and not supported by the arm, and displaced by movement of the arm, optionally the seal comprises a resilient element, and the arm comprises an engagement element which engages the seal with the movement of the arm, optionally the seal comprises a resilient flap.

14. The delivery device of claim 10, wherein the seal comprises a resilient element.

15. The delivery device of claim 1, wherein the valve assembly, on opening of the valve element, provides for a burst of air flow, having a first, initial burst phase followed by a second, extended burst phase, wherein the peak flow rate in the first burst phase has a higher flow rate than the average flow rate in the second burst phase, and the second burst phase is of greater duration than the first burst phase, and
wherein the peak flow rate in the first burst phase is at least 10% greater than that of the average flow rate of the second burst phase as compared across a period ten times longer than the period in which substance is delivered.

16. The delivery device of claim 15, wherein the peak flow rate in the first burst phase is at least 15% greater than that of the average flow rate of the second burst phase.

17. The delivery device of claim 15, wherein the peak flow rate in the first burst phase is at least 20% greater than that of the average flow rate of the second burst phase.

18. The delivery device of claim 1, further comprising:
a housing which includes an aperture through which the actuator of the delivery pump extends.

19. The delivery device of claim 18, wherein the housing further comprises a seal which slideably receives the actuator to prevent air flow from the aperture in the housing.

20. The delivery device of claim 1, wherein the valve assembly provides for a pre-actuation efficiency of less than 5 L/min when the subject is developing an exhalation pressure of 3 kPa.

21. The delivery device of claim 20, wherein the valve assembly provides for a pre-actuation efficiency of less than 1 L/min when the subject is developing an exhalation pressure of 3 kPa.

22. The delivery device of claim 20, wherein the valve assembly provides for a pre-actuation efficiency of 0 L/min when the subject is developing an exhalation pressure of 3 kPa.

23. The delivery device of claim 20, wherein the valve assembly provides for a pre-actuation efficiency of less than 5 L/min when the subject is developing an exhalation pressure of 10 kPa.

24. The delivery device of claim 21, wherein the valve assembly provides for a pre-actuation efficiency of less than 1 L/min when the subject is developing an exhalation pressure of 10 kPa.

25. The delivery device of claim 24, wherein the delivery device is configured to provide at least 90% of the air as delivered into the mouthpiece to the nosepiece when delivered at a flow rate of 50 L/min and an exhalation pressure of 3 kPa.

26. The delivery device of claim 22, wherein the valve assembly provides for a pre-actuation efficiency of 0 L/min when the subject is developing an exhalation pressure of 10 kPa.

27. The delivery device of claim 1, wherein the delivery device is configured to provide at least 80% of the air as delivered into the mouthpiece to the nosepiece when delivered at a flow rate of 50 L/min and an exhalation pressure of 3 kPa.

28. The delivery device of claim 27, wherein the delivery device is configured to provide at least 88% of the air as delivered into the mouthpiece to the nosepiece when delivered at a flow rate of 50 L/min and an exhalation pressure of 3 kPa.

29. The delivery device of claim 1, wherein the delivery pump provides for delivery of substance subsequent to opening of the valve element.

30. The delivery device of claim 29, wherein the delivery pump provides for delivery of substance in a period less than about 250 ms from opening of a sealing member of the valve assembly.

31. The delivery device of claim 30, wherein the delivery a pump provides for delivery of substance in a period less than about 200 ms from opening of the sealing member.

32. The delivery device of claim 30, wherein the delivery pump provides for delivery of substance in a period less than about 150 ms from opening of the sealing member.

33. The delivery device of claim 30, wherein the delivery pump provides for delivery of substance in a period less than about 100 ms from opening of the sealing member.

34. The delivery device of claim 29, wherein the delivery pump provides for delivery of substance commencing less than about 150 ms subsequent to opening of the valve element.

35. The delivery device of claim 34, wherein the delivery pump provides for delivery of substance commencing less than about 100 ms subsequent to opening of the valve element.

36. The delivery device of claim 34, wherein the delivery pump provides for delivery of substance commencing less than about 50 ms subsequent to opening of the valve element.

37. The delivery device of claim 34, wherein the delivery pump provides for delivery of substance commencing less than about 25 ms subsequent to opening of the valve element.

38. The delivery device of claim 34, wherein the delivery pump provides for delivery of substance commencing less than about 15 ms subsequent to opening of the valve element.

39. The delivery device of claim 1, wherein the delivery pump comprises an outlet from which substance is delivered through the nosepiece.

40. The delivery device of claim 39, wherein the delivery pump comprises a substance-containing chamber.

41. The delivery device of claim 39, wherein the outlet is a spray nozzle.

42. A method of delivering substance to a nasal airway of a subject, comprising the steps of:
fitting a nosepiece to a nasal cavity of the subject;
the subject exhaling into a mouthpiece;
providing a delivery device which comprises: a mechanical delivery pump, which comprises an actuator which is manually displaceable to actuate the delivery pump to deliver substance from the nosepiece; and a valve assembly which is fluidly connected to the nosepiece and the mouthpiece, wherein the valve assembly comprises a body element and a valve element movable relative to the body element between closed and open configurations by manual displacement of the actuator of the delivery pump, wherein the body element includes a pivot, and the valve element comprises an arm having a first end pivotal connected to the body element and configured to pivot between the closed and open configurations; and manually displacing the actuator of the delivery pump to move the valve element of the valve assembly relative to the body element of the valve assembly between closed and open configurations and provide an air flow through the nosepiece simultaneously with delivery of substance.

43. A nasal delivery device for delivering substance to a nasal airway of a subject, comprising:

a nosepiece for fitting to a nasal cavity of the subject;

a mouthpiece into which the subject in use exhales;

a mechanical delivery pump, which comprises an actuator which is manually displaceable to actuate the delivery pump to deliver substance from the nosepiece; and a valve assembly which is fluidly connected to the nosepiece and the mouthpiece, wherein the valve assembly comprises a body element and a valve element movable relative to the body element between closed and open configurations by manual displacement of the actuator of the delivery pump to provide for an air flow through the nosepiece simultaneously with delivery of substance;

wherein the body element includes a pivot, and the valve element comprises an arm having a first end pivotally connected to the body element and configured to pivot between the closed and open configurations; and wherein the valve assembly, on opening of the valve element, provides for a burst of air flow, having a first, initial burst phase followed by a second, extended burst phase, wherein the peak flow rate in the first burst phase has a higher flow rate than the average flow rate in the second burst phase, and the second burst phase is of greater duration than the first burst phase.

* * * * *

UNITED STATES PATENT AND TRADEMARK OFFICE
CERTIFICATE OF CORRECTION

PATENT NO. : 10,300,229 B2  
APPLICATION NO. : 14/380827  
DATED : May 28, 2019  
INVENTOR(S) : Per Gisle Djupesland et al.

It is certified that error appears in the above-identified patent and that said Letters Patent is hereby corrected as shown below:

In the Claims

Claim 1, Column 8, Lines 17-19:
"a mechanical delivery puma, which comprises an actuator which is manually displaceable to actuate the delivery pump to deliver substance from the nosepiece;"
Should read:
--a mechanical delivery pump, which comprises an actuator which is manually displaceable to actuate the delivery pump to deliver substance from the nosepiece;--.

Signed and Sealed this
Fifteenth Day of October, 2019

Andrei Iancu
*Director of the United States Patent and Trademark Office*